United States Patent [19]

Caugant et al.

[11] Patent Number: 4,510,613
[45] Date of Patent: Apr. 9, 1985

[54] DIAPHRAGM FOR DEFINING A RADIATION BEAM

[75] Inventors: Jean Caugant; Jacques Dale, both of Paris, France

[73] Assignee: Thomson-CSF, Paris, France

[21] Appl. No.: 489,353

[22] Filed: Apr. 28, 1983

[30] Foreign Application Priority Data

Apr. 30, 1982 [FR] France .................... 82 07522

[51] Int. Cl.³ .................... A61B 6/00; G21K 1/04
[52] U.S. Cl. .................... 378/152; 250/519.1
[58] Field of Search .................... 378/152, 151, 150; 250/519.1

[56] References Cited

U.S. PATENT DOCUMENTS 3,287,561 11/1966 Ingles .................... 378/152
3,622,432 11/1971 McCluer .................... 250/519.1
3,668,402 6/1972 Palermo et al. .................... 378/152

Primary Examiner—Alfred E. Smith
Assistant Examiner—T. N. Grigsby
Attorney, Agent, or Firm—Oblon, Fisher, Spivak, McCelland & Maier

[57] ABSTRACT

The definition diaphragm for the X-ray beam located at the image receiver serves to eliminate part of the stray radiation. According to the invention, the diaphragm comprises a frame and a plurality of partial overlap members each having one portion made from lead rubber, so that it can be turned down perpendicular to the plane of the opening, so that the radial dimensions of the diaphragm are reduced to a minimum. Application is to conventional radiology.

10 Claims, 2 Drawing Figures

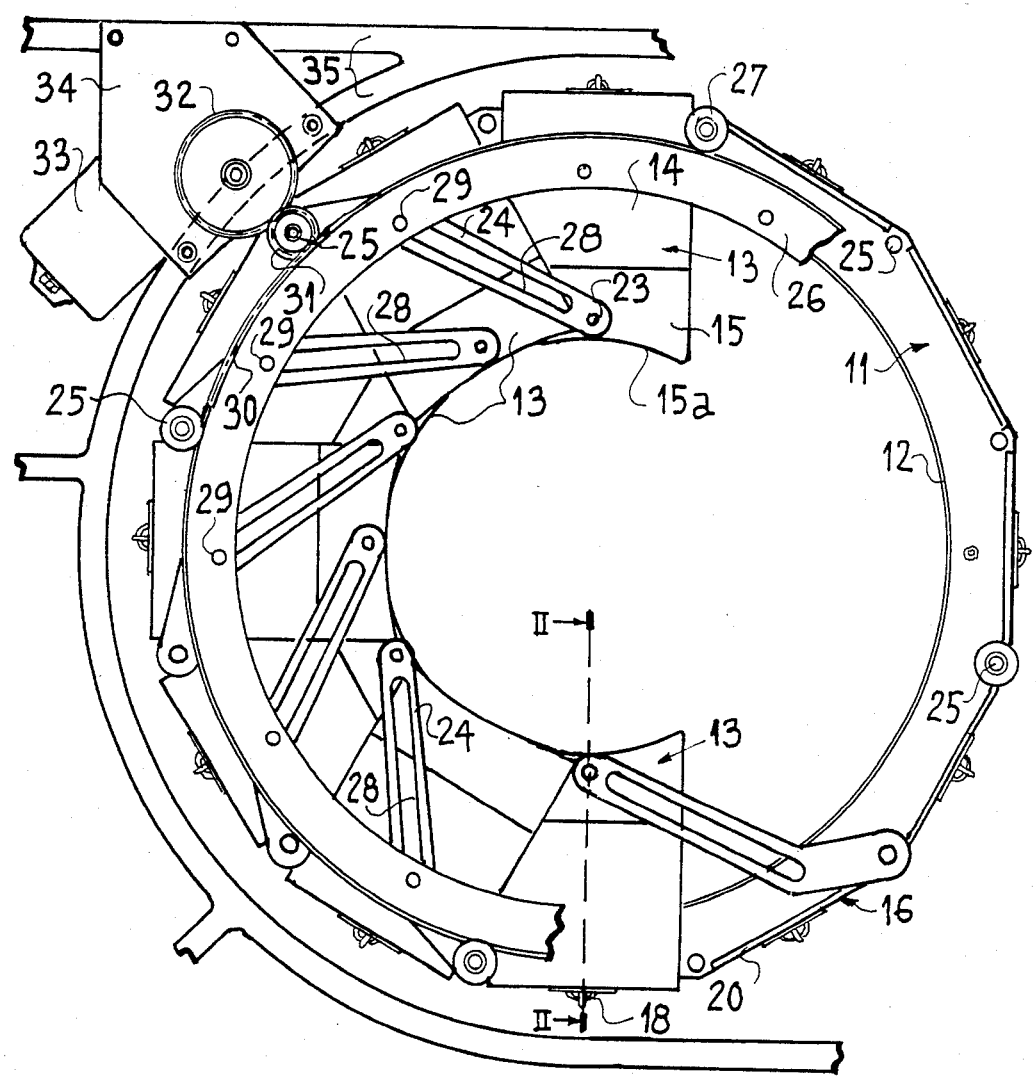
FIG_1

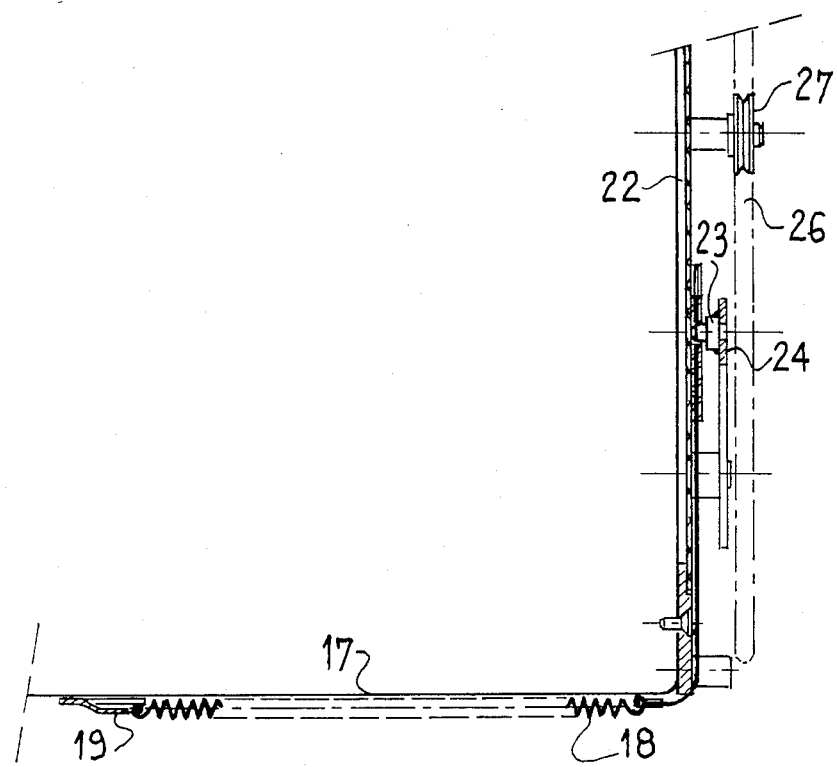
FIG_2

DIAPHRAGM FOR DEFINING A RADIATION BEAM

BACKGROUND OF THE INVENTION

The invention relates to a diaphragm for defining a radiation beam, particularly an X-ray beam, said diaphragm being more particularly intended for the positioning in front of the light amplifier of an X-ray unit.

An X-ray unit comprises an X-ray source transmitting a divergent beam in the direction of a receiver, called an image intensifier. The patient is positioned between the source and the image intensifier. It is known to adjust the width of the beam by means of a diaphragm placed between the source and the patient. This makes it possible to limit the radiation exposure of the patient to what is absolutely necessary for carrying out the diagnosis. Moreover, the image intensifier has a circular reception surface, whose diameter is determined as a function of the maximum aperture of the beam. This beam can be 40 cm. When the beam aperture is limited by the aforementioned diaphragm to smaller dimensions, the corresponding X-ray image only forms on part of the image intensifier surface, whereby said part is always centred. Under these conditions, the image appears in the centre of a stray radiation halo, which is prejudicial to its sharpness and makes it more difficult to interpret. It is therefore important to eliminate that part of the stray radiation surrounding the image, by placing an annular absorbing structure above the unused part of the reception surface of the image intensifier.

SUMMARY OF THE INVENTION

The invention proposes a large diaphragm, which is able to bring about the sought result.

More specifically, the invention relates to a diaphragm for defining a beam, particularly an X-ray beam at the input of an image receiver, such as an image intensifier of the type comprising a frame in which there is an opening and a plurality of elements partly overlapping the said opening, wherein the overlap elements consist of flexible material plates and the rear parts thereof extending beyond the outer edge of the frame are turned down, preferably substantially perpendicular to the plane of the said opening.

The aforementioned diaphragm has a simple, inexpensive construction and the flexibility of the overlap members which can be turned down makes it possible to obtain a device which scarcely has larger dimensions than the diameter of the image intensifier above which it is placed. The addition of such a diaphragm to the X-ray unit consequently does not constitute a nuisance for hospital staff working around the patient.

According to an advantageous feature of the invention, the flexible material plates referred to hereinbefore are made from lead rubber.

BRIEF DESCRIPTION OF THE DRAWINGS

The invention is described in greater detail hereinafter relative to a non-limitative embodiment of a diaphragm and with reference to the attached drawings, wherein show:

FIG. 1 a plan view, which is partly torn away, of a diaphragm according to the invention, certain of the aforementioned overlap members being removed for reasons of clarity.

FIG. 2 a partial section along line II—II of FIG. 1.

DETAILED DESCRIPTION OF A PREFERRED EMBODIMENT

The diaphragm shown in the drawings comprises a frame 11 in which there is a large circular opening 12 and a plurality of members 13, which partly overlap opening 12. Each member 13 is made from a rectangular flexible lead rubber plate 14 and a portion 15 made from a high density material, lead in the present case. Portion 15 is closest to the centre of opening 12 and is therefore extended towards the outside by the flexible material plate 14. Its leading edge 15a is slightly concave, so that the opening of the diaphragm is as close as possible to a circle. The flexibility of the material forming each plate 14 ensures that its rear part extending beyond the outer edge 16 of frame 11 can easily be turned down perpendicular to the plane of opening 12. Thus, the overall dimensions of the diaphragm scarcely exceed those of the image intensifier which it covers. Frame 11 is directly screwed to the upper part of image intensifier 17 and the flexible material plates 14 are kept turned down along the body of the latter by means of respective tension springs 18. Thus, each spring 18 is mounted between the rear part of each plate 14 and a fixed point 19 arranged along the body of image intensifier 17. The outer edge 16 of frame 11 has the same number of rectilinear portions as there are flexible material plates 14. Each rectilinear portion is provided with a chamfer 20, whose length is substantially equal to the width of the corresponding plate 14. This chamfer guides the plate, when the latter moves along the side wall of the image intensifier, during a change of the diaphragm opening. In the present embodiment, the diaphragm has twelve overlap members and frame 11 has consequently the shape of a regular twelve-sided polygon. A plate 22 made from a material which is transparent to X-rays covers opening 12. The overlap members 13 consequently slide on this plate and there is no risk of them scratching the upper surface of the image intensifier.

A description will now be provided of the mechanism making it possible to simultaneously drive the overlap member 13 approximately in accordance with a direction passing through the centre of opening 12. Each overlap member 13 is assembled in articulated manner (articulation axis 23) to a pivoting arm 24 forced to move in a plane parallel to that of opening 12, the arm being articulated about a respective pivot 25 fixed to frame 11 and oriented perpendicular to the surface of opening 12. Thus, there are 12 pivots 25 regularly distributed around frame 11 in the vicinity of the apices of the aforementioned polygon. The pivoting arms 24 are coupled to a ring 26, which rotates coaxially to circular opening 12. Obviously the rotation axis of this ring is of an imaginary nature. Its guidance in rotation is ensured by several pulleys 27, which freely rotate around certain of the pivots 25. The outer circular edge of ring 26 engages in the grooves of these pulleys. Thus, the latter maintain ring 26 in position above pivoting arms 24 and guide the same in rotation. Each arm 24 has a slot perforation 28 and a stud 29 integral with ring 26 engages in each perforation. The outer edge of ring 26 also has a toothed segment 30 engaging with a pinion 31, itself mounted on one of the pivots 25. Pinion 31 meshes with a pinion 32 rotated by means of an electric motor 33. The latter is integral with a plate 34, fixed to a moulded casing 35 in an X-ray unit and surrounding the image intensifier in order to protect the same.

The operation of the diaphragm according to the invention is apparent from the previous description. The rotation of ring 26 pivots all the arms 24 in the same way, due to the cooperation of drive pins 29 and perforations 28. Thus, the overlap members 13 are all displaced in the same way in accordance with a circular arc very close to a radius of opening 12, bearing in mind the position of the pivoting point of an arm 24 relative to the overlap member to which it is coupled. Springs 18 maintain the unused parts of the flexible material plates parallel to the image intensifier casing and ensure a certain tension thereon. It is possible to provide position copying between the diaphragm located with the X-ray source and that described hereinbefore, for which purpose a potentiometer can be mechanically coupled with pinion 31.

Although the invention has been described hereinbefore with reference to specific embodiments, it is not limited thereto and in fact covers all the variants thereof.

What is claimed is:

1. A diaphragm for defining a beam, particularly an X-ray beam at the input of an image receiver such as an image intensifier, comprising a frame in which there is an opening and a plurality of elements partly overlapping the said opening, wherein the overlap elements consist of flexible material plates and the rear parts thereof extending beyond the outer edge of the frame are turned down, preferably substantially perpendicular to the plane of the said opening.

2. A diaphragm according to claim 1, wherein the flexible material plates are made from lead rubber.

3. A diaphragm according to claim 1, wherein the portion of each overlap member which is closest to the centre of the opening is made from a high density material, e.g. lead, said portion being extended towards the outside by one of the aforementioned flexible material plates.

4. A diaphragm according to claim 1, wherein the outer edge of the frame has the same number of rectilinear portions as there are flexible material plates and each rectilinear portion is chamfered in order to guide a plate.

5. A diaphragm according to claim 1, wherein a tension spring is mounted between the rear part of each plate and a corresponding fixed point.

6. A diaphragm according to claim 1, wherein it comprises a mechanism for simultaneously driving the overlap members to follow directions passing through the centre of symmetry of the opening.

7. A diaphragm according to claim 6, of the type having a circular opening, wherein each overlap member is assembled in articulated manner with a pivoting arm, which is forced to move in a plane parallel to that of the opening.

8. A diaphragm according to claim 7, wherein the pivoting arms are coupled to a ring, which rotates coaxially to the circular opening, e.g. between guidance pulleys or the like, which rotate freely on the said frame.

9. A diaphragm according to claim 8, wherein each pivoting arm is provided with a perforation and a drive pin integral with the ring is engaged in said perforation.

10. A diaphragm according to claim 8, wherein the outer edge of the ring has a toothed segment engaging with at least one pinion driven by a motor.

* * * * *